(12) United States Patent
Schoenfisch et al.

(10) Patent No.: US 11,420,986 B2
(45) Date of Patent: Aug. 23, 2022

(54) FUNCTIONALIZED MESOPOROUS SILICA VIA AN AMINOSILANE SURFACTANT ION EXCHANGE REACTION: CONTROLLED SCAFFOLD DESIGN AND NITRIC OXIDE RELEASE

(71) Applicant: The University of North Carolina at Chapel Hill, Chapel Hill, NC (US)

(72) Inventors: Mark H. Schoenfisch, Chapel Hill, NC (US); Robert J. Soto, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 145 days.

(21) Appl. No.: 15/772,759

(22) PCT Filed: Nov. 2, 2016

(86) PCT No.: PCT/US2016/060083
§ 371 (c)(1),
(2) Date: May 1, 2018

(87) PCT Pub. No.: WO2017/079268
PCT Pub. Date: May 11, 2017

(65) Prior Publication Data
US 2018/0319822 A1    Nov. 8, 2018

Related U.S. Application Data

(60) Provisional application No. 62/249,428, filed on Nov. 2, 2015.

(51) Int. Cl.
| | |
|---|---|
| *C07F 7/18* | (2006.01) |
| *A61K 33/00* | (2006.01) |
| *A61K 47/24* | (2006.01) |
| *B01J 20/10* | (2006.01) |
| *B01J 20/28* | (2006.01) |
| *B01J 20/30* | (2006.01) |
| *C01B 21/24* | (2006.01) |
| *C01B 33/18* | (2006.01) |

(52) U.S. Cl.
CPC ............ *C07F 7/188* (2013.01); *A61K 33/00* (2013.01); *A61K 47/24* (2013.01); *B01J 20/103* (2013.01); *B01J 20/28007* (2013.01); *B01J 20/28016* (2013.01); *B01J 20/28083* (2013.01); *B01J 20/3085* (2013.01); *C01B 21/24* (2013.01); *C01B 33/18* (2013.01); *C07F 7/1804* (2013.01); *C01P 2004/61* (2013.01); *C01P 2004/62* (2013.01); *C01P 2004/64* (2013.01); *C01P 2006/17* (2013.01)

(58) Field of Classification Search
CPC ........ C07F 7/188; C07F 7/1804; C01B 33/18; C01B 21/24; B01J 20/3085; B01J 20/28083; B01J 20/28016; B01J 20/28007; B01J 20/103; A61K 47/24; A61K 33/00; C01P 2006/17; C01P 2004/64; C01P 2004/62; C01P 2004/61
See application file for complete search history.

(56) References Cited

U.S. PATENT DOCUMENTS

| | | | |
|---|---|---|---|
| 2006/0018966 A1* | 1/2006 | Lin | ..................... A61K 9/0019 424/484 |
| 2009/0214618 A1 | 8/2009 | Schoenfisch et al. | |
| 2010/0196971 A1 | 8/2010 | Lin et al. | |
| 2014/0065200 A1 | 3/2014 | Schoenfisch et al. | |

FOREIGN PATENT DOCUMENTS

WO    WO 2017/051989 A1    3/2017

OTHER PUBLICATIONS

Burleigh Co-condensation with Organosilanes, J. Phys. Chem. B, p. 9935 (Year: 2001).*
Bourlinos, A.B., et al., "'Side Chain' Modification of MCM-41 Silica through the Exchange of the Surfactant Template with Charged Functionalized Organosiloxanes: An Efficient Route to Valuable Reconstructed MCM-41 Derivatives," J. Phys. Chem. B, 107: 920-925 (2003).
Carpenter, A.W., et al., "Dual Action Antimicrobials: Nitric Oxide Release from Quaternary Ammonium-Funtionalized Silica Nanoparticles," Biomacromolecules, 13(10): 3334-3342 (2012).
PCT International Search Report and Written Opinion of the International Searching Authority for application PCT/US2016/060083 dated Feb. 16, 2017.
European Application No. 16862857.6, Extended European Search Report dated May 9, 2019.
European Application No. 16862857.6, Article 94(3) Communication dated Dec. 16, 2019.
European Application No. 20189710.5, Extended European Search Report dated Oct. 21, 2020.

* cited by examiner

*Primary Examiner* — Matthew P Coughlin
*Assistant Examiner* — Thurman Wheeler
(74) *Attorney, Agent, or Firm* — Alston & Bird LLP

(57) ABSTRACT

Nitric oxide-releasing mesoporous silica nanoparticles (MSNs) were prepared using an aminosilane-template surfactant ion exchange reaction. Initially, bare silica particles were synthesized under basic conditions in the presence of cetyltrimethylammonium bromide (CTAB). These particles were functionalized with nitric oxide (NO) donor precursors via the addition of aminosilane directly to the particle sol, and a commensurate ion exchange reaction between the cationic aminosilanes and CTAB. N-diazeniumdiolate NO donors were formed at the secondary amines to yield NO-releasing silica MSNs. Tuning of the ion exchange-based MSN modification approach allowed for the preparation of monodisperse particles ranging from 30 to 1100 nm. Regardless of size, the MSNs stored appreciable levels of NO (0.4-1.5 μmol/mg) with tunable NO-release durations (1-33 h) dependent on the aminosilane modification. The range of MSN sizes and NO release demonstrate the versatility of this strategy.

15 Claims, 9 Drawing Sheets

FUNCTIONALIZED MESOPOROUS SILICA VIA AN AMINOSILANE SURFACTANT ION EXCHANGE REACTION: CONTROLLED SCAFFOLD DESIGN AND NITRIC OXIDE RELEASE

CROSS-REFERENCE TO RELATED APPLICATION(S)

This application is a US national stage of PCT/US2016/060083, filed Nov. 2, 2016, which claims priority from and the benefit of U.S. Provisional Application No. 62/249,428 filed Nov. 2, 2015, the entire contents of each of which are incorporated by reference in their entirety for all purposes.

STATEMENT OF FEDERAL SUPPORT

This invention was made with government support under Grant Number DMR-1104892 awarded by the National Science Foundation. The government has certain rights in the invention.

BACKGROUND OF THE INVENTION

Nitric oxide (NO), an endogenous diatomic free radical, mediates multiple physiological processes including angiogenesis, blood pressure regulation, wound healing, and the immune response. In vivo, nitric oxide synthase (NOS) enzymes generate NO at concentrations (nM-µM) and kinetics dependent on the enzyme location and purpose. For example, low concentrations of NO generated via calcium-dependent endothelial and neuronal NOS regulate neovascularization and serve roles in neurotransmission. Activation of the inducible NOS isoform by immunological stimuli (e.g., lipopolysaccharide, interferon-γ) causes sustained NO release at high concentrations to eradicate foreign pathogens as part of the innate immune response. The multifaceted roles of endogenous NO are attributable to precise spatiotemporal NO release by cells expressing the NOS enzymes. In addition, NO's short biological lifetime (seconds) restricts its action to <0.5 mm from the point of generation.

Due to NO's overwhelming presence in physiology, the administration of exogenous NO gas represents a potential therapy for many diseases. A significant body of research has focused on the development of donors that store and release NO under specific chemical conditions in order to address the concentration-dependent behavior of NO and avoid challenges associated with the administration of NO directly, such as the need for a pressurized gas cylinder and NO's rapid reaction in biological media. For example, N-diazeniumdiolate NO donors, formed by the reaction of gaseous NO with secondary amines, spontaneously release NO in physiological buffer upon reaction with hydronium ions. This class of molecules has accordingly received attention for biological applications because the breakdown of the NO donor and concomitant NO release occurs at rates dependent on pH, temperature, and the chemical structure of the precursor molecule used for N-diazeniumdiolate formation.

The potential utility of the N-diazeniumdiolate functional group originally inspired research on low molecular weight NO donors. Unfortunately, limited NO capacity and duration generally preclude the use of these small molecule NO donors for therapeutic applications. To enhance NO storage and exert additional control over NO release, much work has focused on the synthesis of N-diazeniumdiolate-modified macromolecular NO-delivery scaffolds, including chitosan oligosaccharides, dendrimers, gold clusters, and silica nanoparticles. With respect to silica, surface grafting, co-condensation, and water-in-oil microemulsion methods have been used to prepare N-diazeniumdiolate-functionalized particles. Silica is attractive as an NO-release scaffold as it is well tolerated (i.e., nontoxic) and readily implemented as a drug delivery vehicle. For example, NO donor-modified silica particles have served as reinforcing fillers for NO-releasing polymeric coatings to promote angiogenesis and wound healing. Such materials have also proven effective as antimicrobial abrasives that may be integrated with oral hygiene technologies.

Despite their value as potential therapeutics, current strategies for synthesizing NO-releasing silica nanoparticles remain limited by challenges associated with altering the physical properties of the particles and the NO release independent of one another. The use of mesoporous silica represents an attractive macromolecular scaffold for enhancing NO storage and release because of the inherently greater and modifiable surface area (>1,000 m$^2$/g) relative to previous nonporous silica systems. Control over pore formation and the silica mesophase is achieved via the synthesis of the nanoparticles around an ordered surfactant aggregate, generally an alkyltrimethylammonium salt, which serves as the structure-directing agent (SDA). Covalent attachment of secondary-amine containing silanes (i.e., NO donor precursors) to mesoporous silica is typically carried out by direct incorporation of the aminosilane into the particle backbone via co-condensation or post-synthetically through surface grafting. In the co-condensation approach, coulombic repulsion between the cationic surfactant molecules and the protonated backbone amines destabilizes the template, resulting in materials with irregular morphology, even at low aminosilane concentrations. Post-synthetic surface grafting (after extracting the SDA) is generally the preferred method for functionalizing mesoporous silica, albeit at the cost of increased synthetic burden. Moreover, the grafting process requires a nonpolar aprotic solvent to avoid irreversible water-induced particle agglomeration, heterogeneous amine distribution, and batch-to-batch irreproducibility.

The synthesis of NO-releasing nanoparticles has been previously reported, but without autonomous control over particle size, NO-release kinetics, and NO storage. Generally, total NO storage for silica-based materials is limited to <0.40 µmol/mg due to low aminosilane incorporation. Limited NO storage often is further compounded by a lack of morphological control and poor synthesis yields.

It is with these shortcomings in mind that the present invention was developed.

BRIEF SUMMARY OF THE INVENTION

An ion exchange reaction with $C_{(5-15)}$alkyltrimethylammonium halides can be used to prepare a diverse selection of monodisperse NO-releasing amine-functionalized mesoporous silica nanoparticles (MSNs) by direct addition of the aminosilane to the particle sol. It is contemplated and therefore within the scope of the present invention that a similar ion exchange approach would be feasible using cetyltrimethylammonium chloride (i.e., an SDA with another halide counterion). Other salts with a range of cation structures are also appropriate for the present invention. Some examples of these include SDAs with chemical structures that accompany the list given below:

a. Linear alkylammonium salts with molecular structures $[C_nH_{2n+1}(CH_3)_3N]^+$ $Br^-$ or $[C_nH_{2n+1}(C_2H_5)_3N]^+$ $Br^-$ where n=8, 10, 12, 14, 16, 18, 20, 22.

b. Geminal salts with general molecular structures $[(C_nH_{2n+1}(CH_3)_2N-(CH_2)_s-N(CH_3)_2-C_mH_{2m-1}]^+$ $Br^-$ where n=m=12, 14, 16, 18, 20, 22 and s=2-12.

c. Divalent surfactants with general molecular structures $[C_nH_{2n+1}(CH_3)_2N-C_mH_{2m+1}(CH_3)_3N]^{2+}$ where n+m=8, 10, 12, 14, 16, 18, 20, 22.

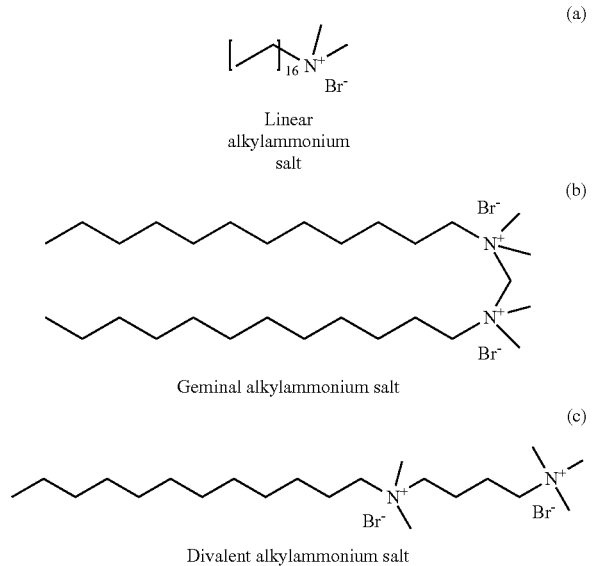

For example, cetyltrimethylammonium bromide (CTAB) has been used to prepare a diverse selection of monodisperse NO-releasing amine-functionalized mesoporous silica nanoparticles (MSNs) by direct addition of the aminosilane to the particle sol. The surface- and pore-bound secondary amines may then be converted to N-diazeniumdiolate moieties to yield the NO-releasing MSNs. The relationships between NO-release kinetics and particle structure (i.e., pore organization, aminosilane modification) have been elucidated via detailed physicochemical analysis of the MSNs.

Ion exchange between cationic organosilanes and alkyltrimethylammonium SDAs represents a new MSN functionalization approach.

Nitric oxide-releasing mesoporous silica nanoparticles with a range of sizes (30, 150, 450, and 1100 nm) were successfully prepared using an aminosilane-CTAB ion exchange approach. The resulting MSNs were well-defined and exhibited a large degree of surface modification, which translated to competitive NO storage with other macromolecular NO donors (e.g., MOFs, RSNOs). Particle NO storage and release kinetics were dependent on both the structure of the pores and the identity of the precursor aminosilane. This invention is the first to detail the dependence of NO-release kinetics on the architectural properties of mesoporous silica.

DETAILED DESCRIPTION OF THE INVENTION

Figure 1:
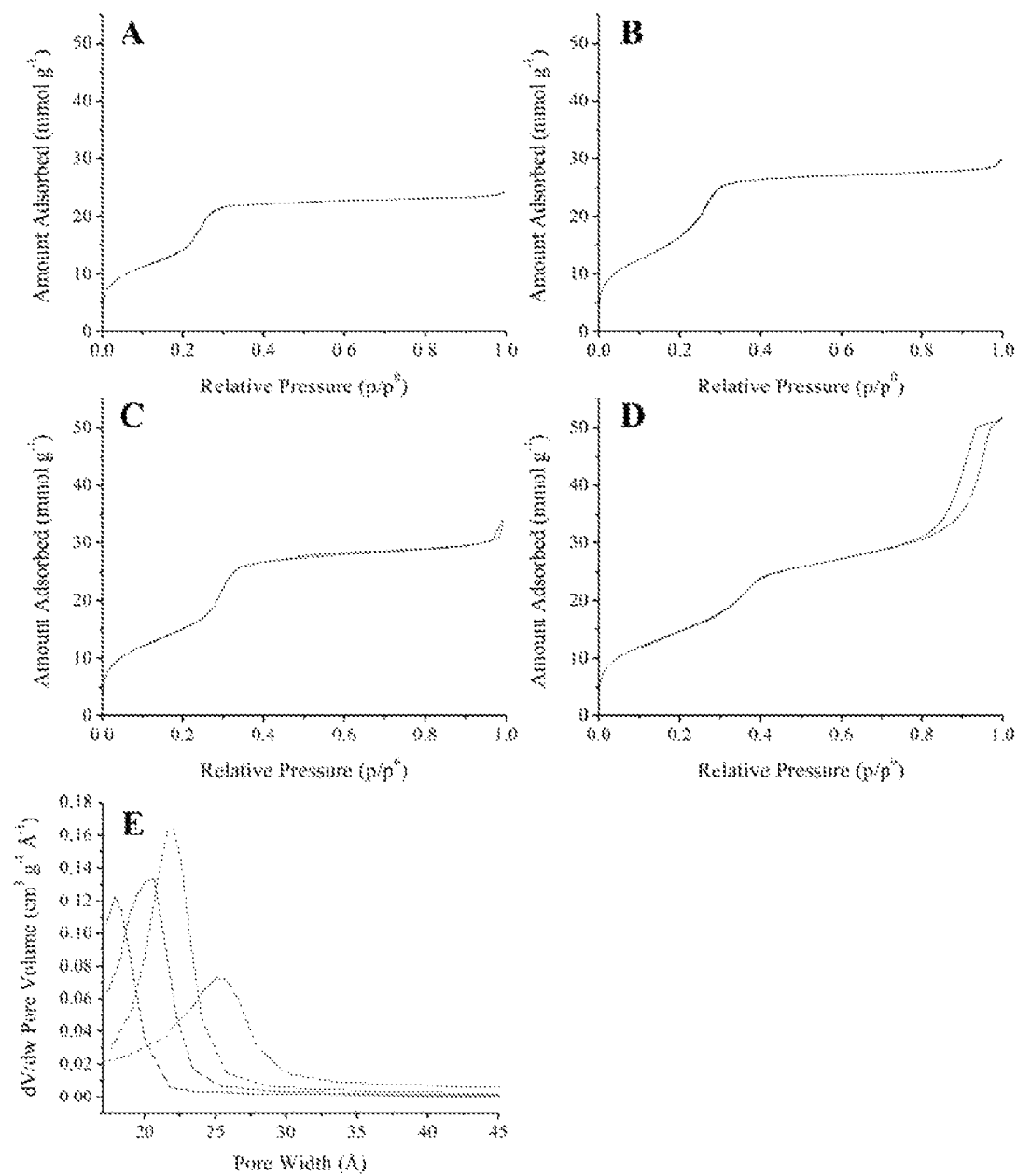
FIG. 1 shows nitrogen adsorption and desorption isotherms for bare (A) 1100; (B) 450; (C) 150; and (D) 30 nm MSNs. The estimated pore width distributions calculated via BJH analysis of the adsorption branch are presented in (E) for the 1100 (black), 450 (blue), 150 (red), and 30 nm (green) particles.

Nitric oxide-releasing silica nanoparticles have demonstrated promise as antimicrobials, but are traditionally limited in terms of their uncontrollable physical properties (e.g., size), low nitric oxide storage, and poor synthesis yields. In an embodiment, the present invention relates to a new preparative strategy for nitric oxide-releasing silica nanoparticles that exploits ion exchange reactions between aminosilanes used for nanoparticle functionalization and the cationic template surfactant that controls nanoparticle formation. When compared with previous synthesis protocols, the efficiency of this process allows for autonomous control over particle physicochemical properties including nitric oxide storage, nitric oxide-release kinetics, and particle size. Synthesis yields as high as 0.8 grams also represent a significant advantage over other strategies (0.01-0.1 grams) and the flexibility of this process for particle modification with several functional cationic organosilanes was demonstrated. Prior to this invention, mesoporous silica materials could be functionalized through either co-condensation or surface grafting. Modification via ion exchange reactions holds the following advantages over pre-existing methods: 1) Consistent material morphology regardless of aminosilane incorporation (not possible with co-condensation, difficult and irreproducible with surface grafting) 2) One-pot synthesis of amine-functionalized materials (not possible with surface grafting) 3) Insensitive to ambient humidity (not possible with surface grafting) 4) Streamlined material synthesis and aminosilane incorporation is reproducible.

Additionally, other disadvantages of the prior surface grafting method results in low nitrogen incorporation and NO storage (see table 8 for typical values). Moreover, surface grafting has a water sensitive step that often results in irreproducible percentage of nitrogen incorporation and uneven amine special distribution. Co-condensation drawbacks include generating core amines that tend to be inaccessible for further chemical modification and no to little morphological control.

Prior art synthesis of NO-releasing nanoparticles suffers from the drawback of lacking autonomous control over particle size, NO-release kinetics, and NO storage. Generally, total NO storage for silica-based materials is limited to <0.40 µmol/mg due to low aminosilane incorporation. Limited NO storage often is further compounded by a lack of morphological control and poor synthesis yields. Accordingly, the present invention relates to a new method of synthesis wherein mesoporous silica was selected as a new scaffold in an attempt to exert greater control over particle NO-release properties. Mesoporous silica nanoparticles were prepared via a supramolecular liquid-crystal templating approach. Cationic, amphiphilic CTAB aggregates were used as the structure-directing agent for particle synthesis. The synthesis of four different sized MSNs was achieved using tetraethylorthosilicate (TEOS) by altering the reaction temperature and reactant concentrations (See Table 1). For example, by employing lower temperatures (on the order of 20-25° C.) lesser amounts of water (on the order of 25 M) and a higher ratio of amine to alkyltrimethylammonium halide, one is able to attain larger particle sizes, whereas higher temperatures (on the order of 65-70° C.), higher water concentration (on the order of 55 M) and a smaller ratio of amine to alkyltrimethylammonium halide allows one to achieve smaller particle sizes. Thus, on the whole, to generate the particle sizes of the present invention, the temperature ranged from about 20-70° C., the water concentration ranged from about 25-55M, the amine concentration ranged from about 0.25 M to about 0.55 M, and the alkyltrimethylammonium halide ranged from about 2 mM to 5.5 mM.

Surfactant was removed by ion exchange in ethanolic hydrochloric acid (HCl) to yield the bare mesoporous scaffold. While other methods (e.g., calcination) have been used for CTAB removal, irreversible particle agglomeration often results. Surfactant removal from the MSNs after agitation in HCl was evaluated using elemental analysis. The measured nitrogen wt % for the bare particles was <0.2% in all cases (indicating complete CTAB removal), with the exception of the 150 nm system (~1.11%). The significant nitrogen content was attributed to trapped ammonia, since the low carbon content (5.48±1.00%) did not reflect the presence of CTAB (~80.3% carbon by mass).

The surface areas and pore sizes of the unmodified MSNs were calculated from the corresponding nitrogen sorption isotherms (FIG. 1). Each of the physisorption isotherms exhibited steep inflections at ~0.2-0.4 $p/p^0$ and >0.8 $p/p^0$ corresponding to capillary condensation of nitrogen in the particle mesopores and inter-particle volumes, respectively. All isotherms were classified as Type IV isotherms without hysteresis according to the conventions adopted by the International Union of Pure and Applied Chemistry (IUPAC). Nitrogen gas adsorption/desorption on CTAB-templated mesoporous silica has consistently yielded similar results. Importantly, MSN surface areas calculated using the Brunauer-Emmett-Teller (BET) method exceeded 1000 $m^2/g$ in all cases (Table 1) regardless of particle size. Pore sizes were evaluated using Barrett-Joyner-Halenda (BJH) analysis of a portion of the nitrogen adsorption branch (see FIG. 1e) and yielded calculated pore widths in the range of 19.5-23.6 Å, which are comparable to those reported in the literature.

The particles were modified with secondary amines by direct organosilane addition to the reaction solution following completion of the particle synthesis reaction (<2 h as determined by dynamic light scattering). Exemplary organosilanes include cationic organosilanes such as N-(6-aminohexyl)aminopropyltrimethoxysilane (AHAP3), N-[3-(trimeth-oxysilyl) propyl]diethylenetriamine (DET3), N-(2-aminoethyl)-3-aminopropyltrimethoxysilane (AEAP3) and methyl aminopropyl-trimethoxysilane (MAP3). Other cationic organosilanes that might potentially be used in the present invention include one or more of N-(2-aminoethyl) aminopropyltrimethoxysilane, N-methylaminopropyltrimethoxysilane, N-(6-aminohexyl)aminopropyltrimethoxysilane, N-(6-aminohexyl)aminomethyltrimethoxysilane, 3-aminopropyltrimethoxysilane, 3-(trimethoxysilylpropyl) diethylenetriamine, N-(2-aminoethyl)aminoundecyltrimethoxysilane, aminoethylaminomethyl)phenethyltrimethoxysilane, and mixtures thereof.

Residual surfactant SDA was removed in a subsequent step, similar to unmodified particles. The aminosilane N-(2-aminoethyl)-3-aminopropyltrimethoxysilane (AEAP3) was selected to optimize this process, initially using the largest (1100 nm) particles. Generally, the ion exchange process can be optimized by evaluating nitrogen incorporation (measured using an elemental analyzer) with respect to the aminosilane concentration. Additionally, the pH of the pre-

TABLE 1

Synthesis conditions and nitrogen physisorption data for MSNs of varying size.[a]

| Particle Size | [H$_2$O] (M) | [NH$_3$] (M) | [CTAB] (nM) | Reaction Volume (mL) | Temperature (° C.) | Specific Surface Area (m$^2$ g$^{-1}$)[b] | Pore Width (Å)[c] | Nitrogen wt %[d] |
|---|---|---|---|---|---|---|---|---|
| 30 nm | 54.5 | 0.267 | 5.30 | 150 | 68 ± 1 | 1290 ± 90 | 23.6 ± 2.3 | ≤0.01 |
| 150 nm | 39.4 | 0.267 | 5.30 | 150 | 38 ± 1 | 1170 ± 80 | 21.9 ± 0.6 | 1.11 ± 0.12 |
| 450 nm | 35.0 | 0.267 | 5.30 | 150 | 23 ± 1 | 1280 ± 120 | 20.4 ± 0.2 | 0.13 ± 0.06 |
| 1100 nm | 25.5 | 0.521 | 2.20 | 350 | 23 ± 1 | 1170 ± 70 | 19.5 ± 0.3 | ≤0.01 |

[a]Error bars represent standard deviation for n >3 separate syntheses.
[b]Determined by BET analysis of the nitrogen sorption isotherms (0.05 < $p/p^0$ < 0.20).
[c]Calculated via BJH analysis of the nitrogen adsorption isotherm ($p/p^0$ < 0.60).
[d]Nitrogen wt % measured by elemental analysis.

cursor solution (i.e., the particle synthesis solution) may need to be altered to ensure protonation of the aminosilane reagent.

Figure 2:
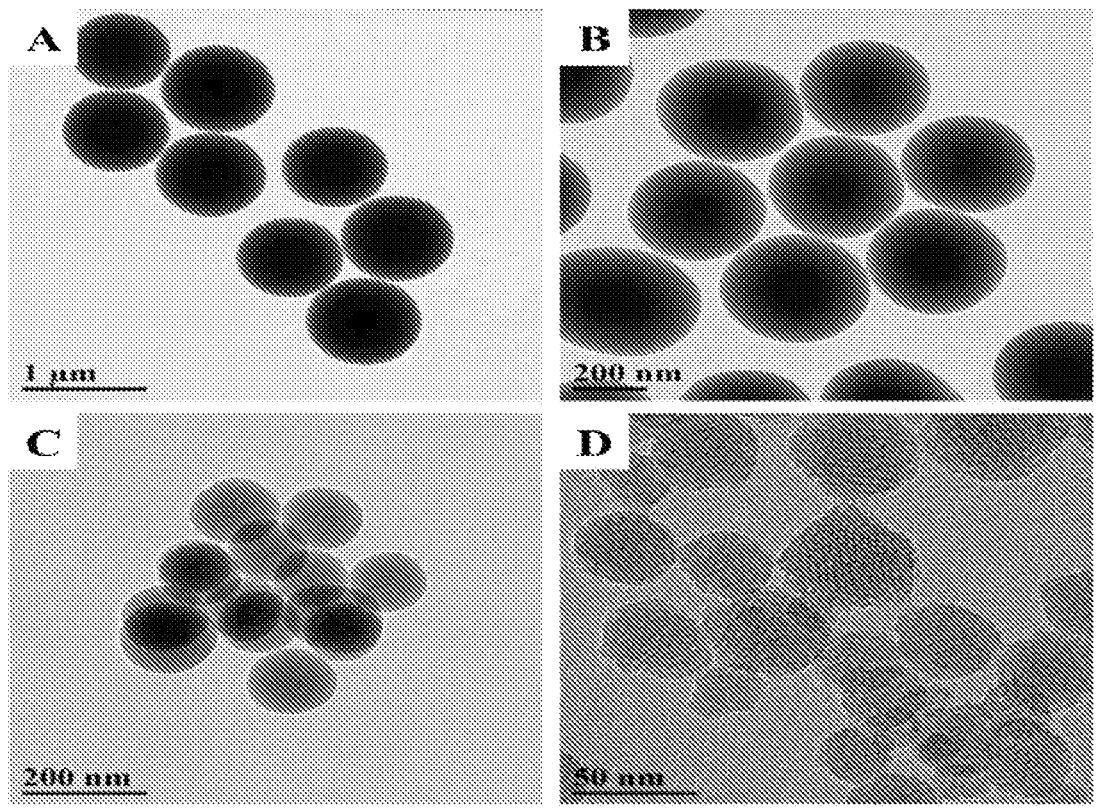
FIG. 2 shows transmission electron micrographs of (A) 1100; (B) 450; (C) 150; and (D) 30 nm AEAP3-modified mesoporous silica nanoparticles.

As expected, elevated nitrogen compositions and lower specific surface areas were observed upon increasing the concentration of AEAP3 in the reaction (Table 2). At the highest AEAP3 concentration presented in Table 2 (11.5 mM), particles retained excellent sphericity and morphology (FIG. 2a) as indicated by transmission electron microscopy (TEM). At this concentration, a maximum nitrogen content of 4.87±0.04 wt %, was measured, suggesting incorporation of AEAP3 to the MSNs rather than the formation of new, discrete AEAP3-based particles. Undesirable particle agglomeration was routinely noted at greater AEAP3 concentrations (>14.3 mM). Inter-particle bridging was occurring at these higher concentrations, revealing a practical maximum in the attainable aminosilane incorporation (See Figure S1). Pore size analysis of the nitrogen adsorption isotherms indicated a clear decrease in mesopore volume with increasing AEAP3 concentration, while the pore width remained invariable (p>0.50). At AEAP3 concentrations at or exceeding 5.7 mM, the gas sorption isotherm abruptly transitioned from a type IV to a type I isotherm, consistent with bound organic groups on the silica network. Taken together, these data indicate AEAP3 infiltration of the particle mesopores at AEAP3 concentrations <11.5 mM.

synthesize smaller AEAP3 particles. The TEOS:aminosilane ratio that was tested was from 1.26:1.00 to 12.84:1.00. Regardless of the intended size, this approach resulted in well-defined nanomaterials (FIG. 2b-d). Dynamic light scattering (DLS) analysis of aqueous MSN dispersions (Table 3) supported TEM observations. The low observed polydispersity indices (PDIs; 0.12, 0.02, and 0.04 for the 30, 150, and 450 nm particles, respectively) affirmed narrow particle size distributions. In a separate embodiment, the four particle systems with nominal diameters of 30, 150, 450, and 1100 nm were prepared with PDIs of 0.17, 0.05, 0.02, and ~0.1, respectively. The DLS/TEM data also provided evidence for covalent bonding of aminosilanes to the particle surface, rather than the formation of discrete entities and likely large agglomerates. Elemental analysis confirmed aminosilane incorporation (>4.50% N) for each particle system, with the 150 nm MSNs exhibiting the greatest nitrogen composition (5.91% N). Of note, the increased nitrogen observed for the 150 nm MSNs is likely due to the large amount of nitrogen in the bare 150 nm MSNs (1.11±0.12% N) and did not reflect improved aminosilane incorporation.

TABLE 3

Physicochemical characterization of AEAP3-fonctionalized MSNs of varying size.[a]

| Geometric Diameter (nm)[b] | Z-average Size (nm)[c] | PDI[c] | Nitrogen wt %[d] | Specific Surface Area ($m^2$ $g^{-1}$)[e] | Pore Width (Å)[f] |
|---|---|---|---|---|---|
| 36 ± 8 | 74 ± 6 | 0.12 ± 0.06 | 4.65 ± 0.19 | 210 ± 40 | 25.1 ± 1.1 |
| 149 ± 13 | 223 ± 17 | 0.02 ± 0.01 | 5.91 ± 0.13 | 69 ± 13 | 24.8 ± 0.6 |
| 450 ± 50 | 564 ± 66 | 0.04 ± 0.02 | 5.07 ± 0.10 | 68 ± 20 | 21.5 ± 0.8 |
| 1110 ± 210 | n/a[g] | n/a[g] | 4.87 ± 0.04 | 3 ± 1 | n/a[h] |

[a]Error bars represent standard deviation for n > 3 separate syntheses.
[b]Estimated using electron micrographs.
[c]Measured via dynamic light scattering.
[d]Nitrogen wt % measured by elemental analysis.
[e]Determined by BET analysis of the nitrogen sorption isotherms (0.05 < $p/p^0$ < 0.20).
[f]Calculated via BJH analysis on the nitrogen adsorption isotherm ($p/p^0$ < 0.60).
[g]Particle sedimentation interfered with DLS measurement.
[h]Pore width could not be calculated from the adsorption isotherm.

TABLE 2

Characterization of AEAP3-modified 1100 nm mesoporous silica particles as a function of reaction aminosilane concentration.[a]

| [AEAP3] (mM) | Specific Surface Area ($m^2$ $g^{-1}$)[b] | Cumulative Pore Volume ($cm^3$ $g^{-1}$)[c] | Pore Width (Å)[c] | Nitrogen wt %[d] |
|---|---|---|---|---|
| 0 | 1200 ± 70 | 0.47 ± 0.09 | 19.5 ± 0.3 | ≤0.01 |
| 1.4 | 790 ± 60 | 0.13 ± 0.02 | 19.4 ± 0.7 | 2.41 ± 0.25 |
| 2.9 | 520 ± 130 | 0.05 ± 0.01 | 20.0 ± 0.7 | 3.38 ± 0.41 |
| 5.7 | 5 ± 1 | 0.01 ± 0.00 | 20.7 ± 2.0 | 4.38 ± 0.33 |
| 11.5 | 3 ± 1 | 0.00 ± 0.00 | N.D.[e] | 4.87 ± 0.04 |

[a]Error bars represent standard deviation for n > 3 separate syntheses.
[b]Determined by BET anaylysis of the nitrogen sorption isotherms (0.05 < $p/p^0$ < 0.20).
[c]Calculated via BJH analysis of the nitrogen adsorption isotherm ($p/p^0$ < 0.60).
[d]Nitrogen wt % measured by elemental analysis.
[e]Pore width could not be calculated from the adsorption isotherm.

Figure 3:
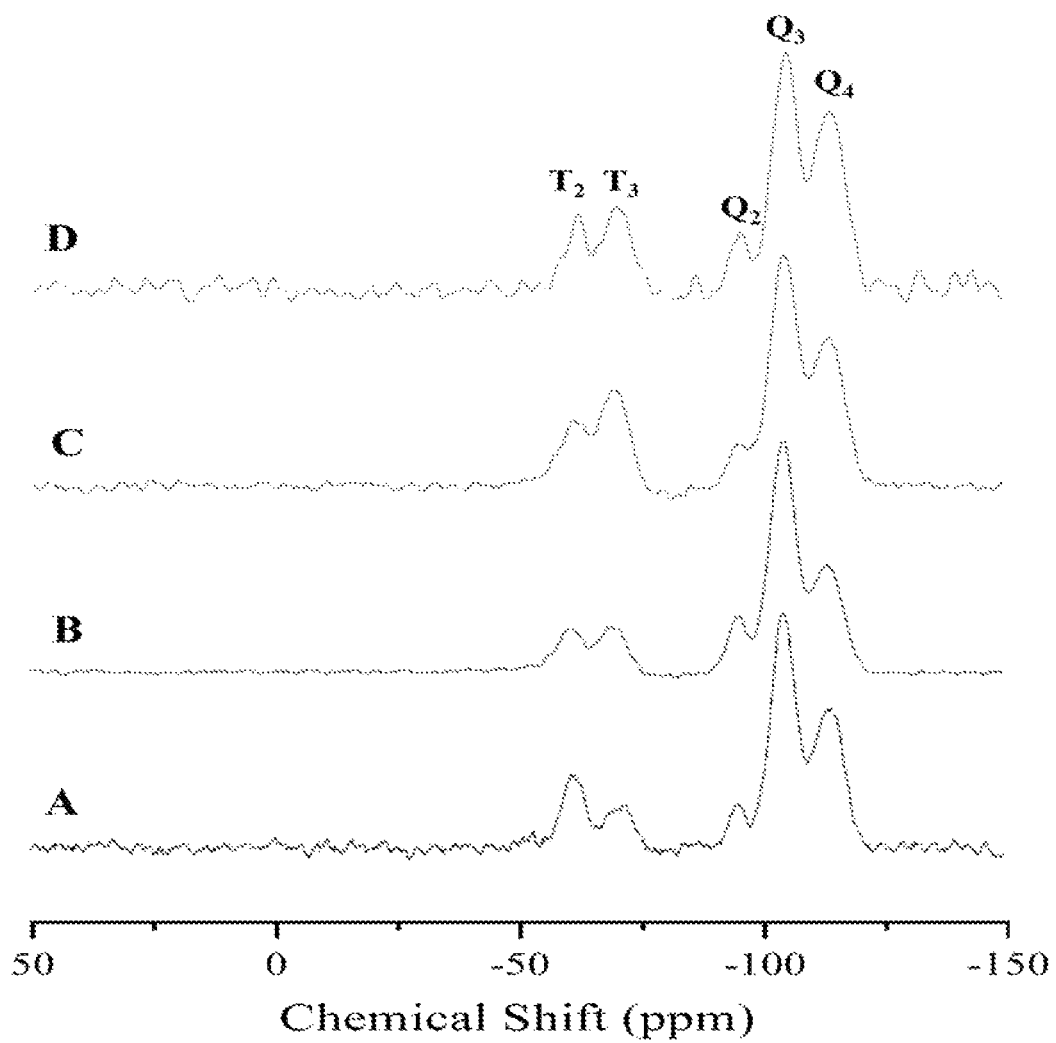
FIG. 3 shows solid-state CP/MAS $^{29}$Si NMR spectra of (A) 1100; (B) 450; (C) 150; and (D) 30 nm AEAP3-modified particles.

Based on the results for the 1100 nm particles, the optimal TEOS:aminosilane molar ratio of 1.56:1.00 was used to While significant particle nitrogen content was measured by elemental analysis, solid-state cross-polarization ($^1$H/$^{29}$Si)/magic angle spinning (CP/MAS) nuclear magnetic resonance spectroscopy (NMR) provided evidence for covalent attachment of AEAP3 to the inorganic TEOS backbone (FIG. 3). The Q-band peaks at −94, −103, and −112 ppm were assigned to backbone Si atoms present as geminal silanol (Q2), lone silanol (Q3), and siloxane (Q4) species, respectively. The T-band, indicative of the bound organosilane (AEAP3), consisted of peaks at −60 and −69 ppm that were assigned to $T_2$ and cross-linked $T_3$ species, respectively. The prevalence of cross-linked surface-bound aminosilanes is attributed to the large water concentration (>20 M) in the reaction mixtures, that drives condensation between aminosilanes. For comparison, MCM-41 materials produced through post-synthetic surface grafting in anhydrous solvents are primarily bidentate $T_2$ species and exhibit limited cross-linking ($T_3+T_3'$).

NITRIC OXIDE RELEASE: After confirming covalent aminosilane attachment, AEAP3-modified particles were functionalized with N-diazeniumdiolate moieties by reaction with NO gas at high pressure in the presence of sodium methoxide. Nitric oxide release was evaluated in real-time via chemiluminescent analysis of the NO-releasing particles in physiological buffer (PBS, pH 7.4) at 37° C. (Table 4). Upon immersion into aqueous solution the AEAP3/NO MSNs were characterized by a large instantaneous NO flux corresponding to reaction of the proton-labile N-diazeniumdiolate with water to generate NO. Despite large total NO storage (>0.8 µmol/mg) for all four particle systems, total NO storage (p<0.01), NO-release half-lives (p<0.01), and release durations (p=0.02) were unexpectedly diverse. The 1100 nm particles exhibited large NO storage (1.41 µmol/mg) and rapid release (t½=25.6 min). Similarly, the 30 nm AEAP3/NO particles released their total NO payload rapidly (t½=27.4 min) but stored only a fraction of the NO measured for the 1100 nm particles ([NO]t=0.88 µmol/mg). While the 450 nm MSNSs were characterized with low NO storage (0.82 µmol/mg), they were associated with the longest NO-release half-life (88.2 min). Relative to the 1100 nm AEAP3/NO particles, the 150 nm MSNs exhibited comparable NO storage (1.30 µmol/mg) but intermediate NO-release rates (t½=41.9 min).

(lattice constant a=43.1±1.5 Å). While the absence of higher-order peaks indicated only modest mesoscopic ordering, the scattering profile consisted of the prominent structural lines for MCM-41-type (hexagonal) silica. In contrast to the observed MCM-41 structure for the largest particles, the scattering profile for the 30 nm MSNs alluded to an alternative mixed pore structure. Analysis of the smallest particles revealed three scattering peaks: 100 (0.155 Å$^{-1}$), 200 (0.301 Å$^{-1}$), and 300 (0.552 Å$^{-1}$), typical of lamellar (layered) pore ordering. The appearance of the 300 reflection represented a high degree of pore ordering; this peak is seldom observed for lamellar mesoporous silica. However, the 200 reflection was relatively broad, suggesting that the pore structure for the 30 nm particles was an intermediate product (i.e., between lamellar and hexagonal). The electron micrographs for the 30 nm MSNs (FIG. 2d) were in good agreement with the scattering data and provided evidence

TABLE 4

Chemiluminescent NO release measurements in physiological buffer (PBS, pH 7.4, 37° C.) from AEAP3/NO MSNs of varying size.$^a$

| Particle Size (nm) | $[NO]_{max}$ (ppm mg$^{-1}$)$^b$ | $t_{1/2}$ (min)$^c$ | $t_d$ (h) | $[NO]_t$ (µmol mg$^{-1}$) | N-Diazeniumdiolate Formation Efficiency (%) |
|---|---|---|---|---|---|
| 30 | 18.7 ± 2.2 | 27.4 ± 8.9 | 12.2 ± 3.0 | 0.88 ± 0.05 | 26.6 ± 1.8 |
| 150 | 22.6 ± 4.4 | 40.7 ± 11.0 | 16.7 ± 1.4 | 1.30 ± 0.11 | 30.9 ± 2.7 |
| 450 | 6.6 ± 1.8 | 88.2 ± 10.5 | 14.0 ± 0.3 | 0.82 ± 0.08 | 22.8 ± 2.3 |
| 1100 | 32.8 ± 9.8 | 25.6 ± 5.0 | 11.1 ± 0.7 | 1.41 ± 0.19 | 40.7 ± 5.2 |

$^a$Error bars represent standard deviation for n > 3 separate syntheses.
$^b$Maximum instantaneous NO concentration.
$^c$Half-life of NO release.
$^d$NO-release duration; time required for NO concentrations to reach <10 ppb mg$^{-1}$.
$^e$Total NO release.
$^f$Calculated using total NO release and nitrogen wt % determined by elemental analysis (Table 3) according to equation provided in Supporting Information.

The difference in NO-release kinetics between particle systems was not anticipated, as all particles were functionalized with the same N-diazeniumdiolate precursor (AEAP3). To shed further light on these effects, total NO release from the AEAP3/NO particles were compared to the degree of nitrogen incorporation measured by elemental analysis (Table 3) to determine N-diazeniumdiolate formation efficiencies. As expected based on the NO release data, the 1100 nm MSNs exhibited the greatest NO donor formation efficiency (40.7%), far greater than that reported by others (<27%). The NO donor formation efficiencies for the other three particle sizes were calculated at 23-31%.

The wide range of NO-release kinetics (half-lives 27-88 min) suggested additional factors were influencing the NO release. Without being bound by theory, it was hypothesized that the structure and ordering of the particle pore network may account for these variations, as a link between mesoscopic ordering and diffusion-based drug release has been demonstrated previously. For example, decreased organization may impede sodium methoxide access to pore-bound secondary amines, hindering N-diazeniumdiolate formation. As an extension of the same logic, altered water diffusion into the pores would give rise to differences in NO-release kinetics between AEAP3/NO MSNs of different size. Powder small-angle X-ray scattering (SAXS) was used to assess pore ordering of the bare MSNs.

Figure 4:
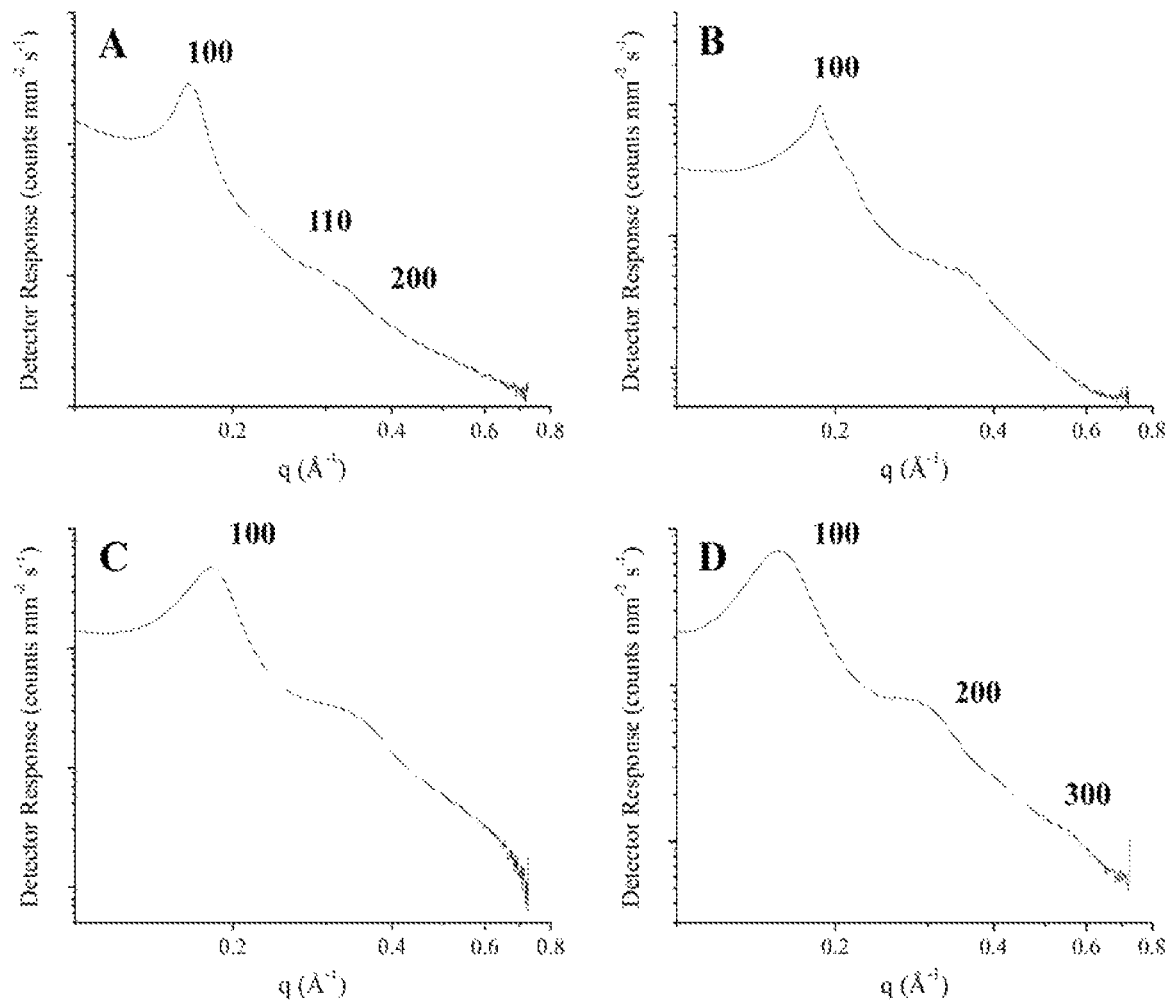
FIG. 4 shows small-angle X-ray scattering profiles for (A) 1100; (B) 450; (C) 150; and (D) 30 nm MSNs.

The SAXS profile for the 1100 nm MSNs (FIG. 4a) exhibited an intense scattering peak at 0.170 Å$^{-1}$ (2θ=2.41 o; hkl 100) and two weaker, larger-angle peaks in the scattering profile were assigned to the 110 (0.292 Å$^{-1}$) and 210 (0.339 Å$^{-1}$) reflections indexed on a hexagonal lattice for both pore structures. X-ray scattering patterns obtained for the 150 and 450 nm particles were representative of a greater degree of pore disorder. Other than the 100 line, only a broad peak centered at ~0.32 Å$^{-1}$ appeared in both scattering profiles. The absence of the 300 reflection suggests decreased pore organization for both particle systems. Indeed, both scattering profiles implied mesopore arrangements between hexagonal and lamellar structures. While pore disorder was not as extensive for 150 nm particles, the skewed 100 peak for the 450 nm MSNs was evidence for a more heterogeneous pore structure. In fact, the irregular peak shape was likely the superimposition of two separate low order reflections.

Particle x-ray scattering data provided insight into the relationship between MSN pore structure and NO-release kinetics. For the largest 1100 nm particles, the ordered hexagonal pore system that was elucidated via SAXS analysis likely allows for unrestricted pore access by sodium methoxide and water, resulting in large NO storage and rapid NO release, respectively. The 150 and 450 nm particles were capable of more sustained NO release due to mixed and disordered pore structure. In contrast, the 30 nm MSNs exhibited rapid NO release resulting from a highly ordered structure that was largely lamellar in character. The lower NO storage (0.88 µmol/mg), unaccounted for by the lamellar pore structure, is likely due to poor dispersal of the 30 nm AEAP3 particles in the N-diazeniumdiolate reaction. Of note, SAXS analysis of the amine-modified particles was also carried out with the results shown in FIG. 8. The scattering profiles of the amine-functionalized particles each exhibited similar pore ordering to their corresponding bare MSNs, although the peaks were broader and lower in intensity, corresponding to pore-filling by the aminosilanes.

ORGANOSILANE MODIFICATION: While aminosilanes are highly reactive with the silanol groups that populate the surface of silica nanoparticles, they also readily undergo hydrolysis and auto-condensation in aqueous conditions to form new, discrete entities. For this reason, addition of organosilane directly to the colloidal sol (i.e., particle reaction mixture) generally yields amorphous materials with heterogenous functional group distribution. Post-synthetic grafting approaches thus require water removal from the reaction mixture to avoid undesirable particle agglomeration.

Figure 5:
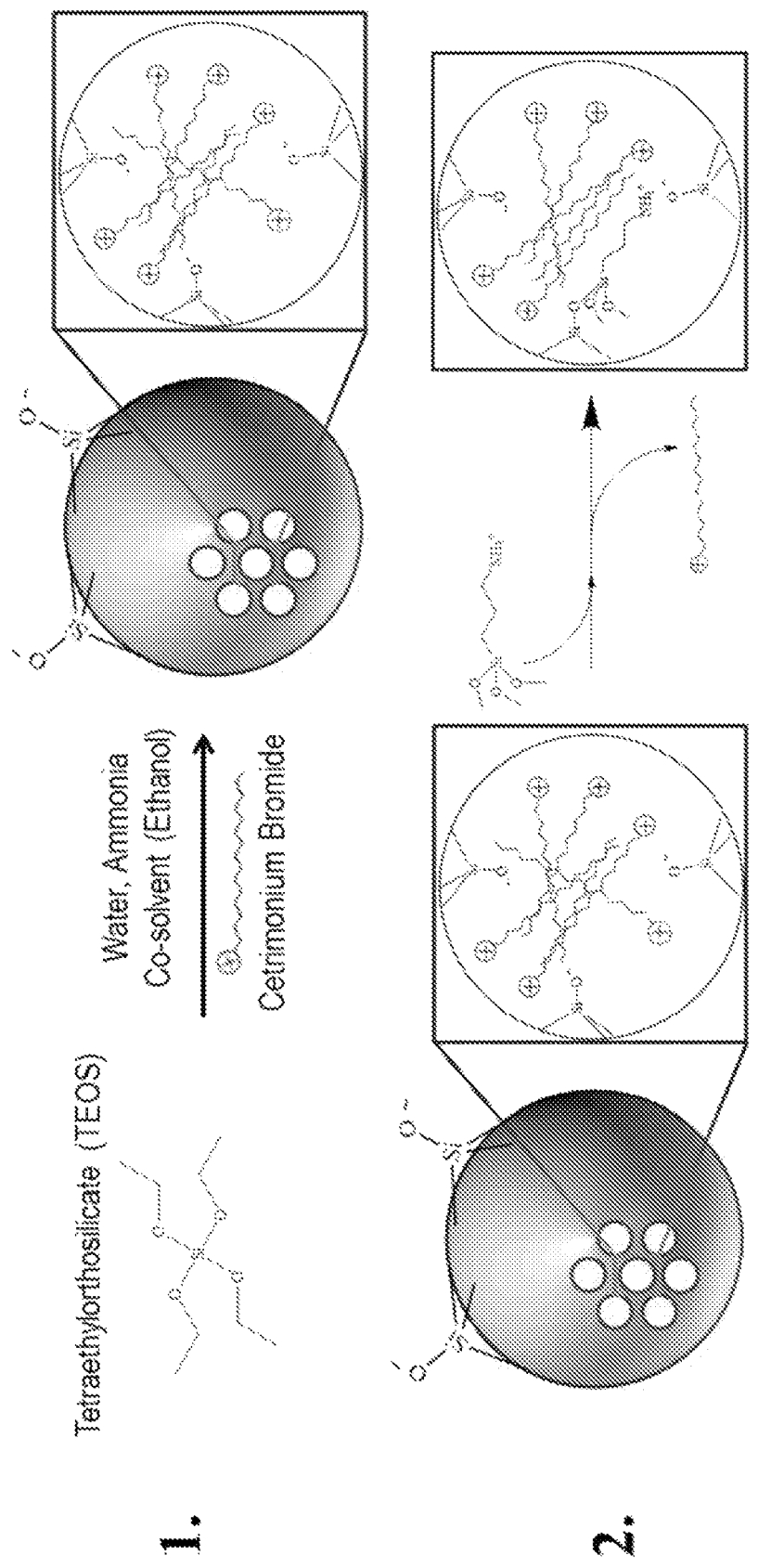
FIG. 5 shows a two-step synthetic scheme to generate MSN functionalization with aminosilanes. The first part involves base-catalyzed synthesis of bare mesoporous silica scaffold. The second part of the scheme shows a proposed mechanism for MSN functionalization with aminosilanes. Positively charged aminosilanes undergo ion exchange with the template surfactant to stabilize anionic silanol species anchored to the mesopore walls.

In addition to anhydrous conditions, efficient particle modification is contingent upon successful removal of the pore-resident surfactant prior to reaction with aminosilanes, as the positively charged template molecule stabilizes the anionic surface silanols and may impede diffusion of external species into the pores. Others have previously exploited the stability of the surfactant CTAB template for selective derivatization of the outer and inner mesoporous silica surfaces using a step-by-step functionalization approach. In an embodiment, the present invention relates to a large degree of particle functionalization wherein the aminosilanes likely displaced CTAB before undergoing any auto-condensation. Without being bound by theory, it is postulated that this phenomenon might be due to an ion-exchange process between the surfactant and protonated aminosilanes (FIG. 5). Others have described ion exchange between cationic species (metal ions and aminosilanes, respectively) and the CTAB template as a method for particle modification. In these cases, the uncalcined (i.e., CTAB-containing) silica was modified in a separate reaction rather than a one-step procedure.

In an embodiment, the present invention relates to MSN modification with cationic species, showing that cationic species retain their particle morphology. Using the 150 nm particle system, the MSNs were functionalized with either isobutyl(trimethoxy)silane (BTMS) or (3-mercaptopropyl) trimethoxysilane (MPTMS) at concentrations equal to those employed for the 150 nm AEAP3 particles. As the colloidal sol is formed under basic conditions, the BTMS alkyl groups remain neutral whereas a significant fraction of the MPTMS side chains would exist as the anionic thiolate species (pKa~10), in both cases preventing ion exchange. 3-aminopropyltriethoxysilane (APTES) was used as a positive control, as APTES is similar in size to BTMS and MPTMS but should undergo efficient ion exchange with CTAB due to the presence of a basic primary amine.

Figure 6:
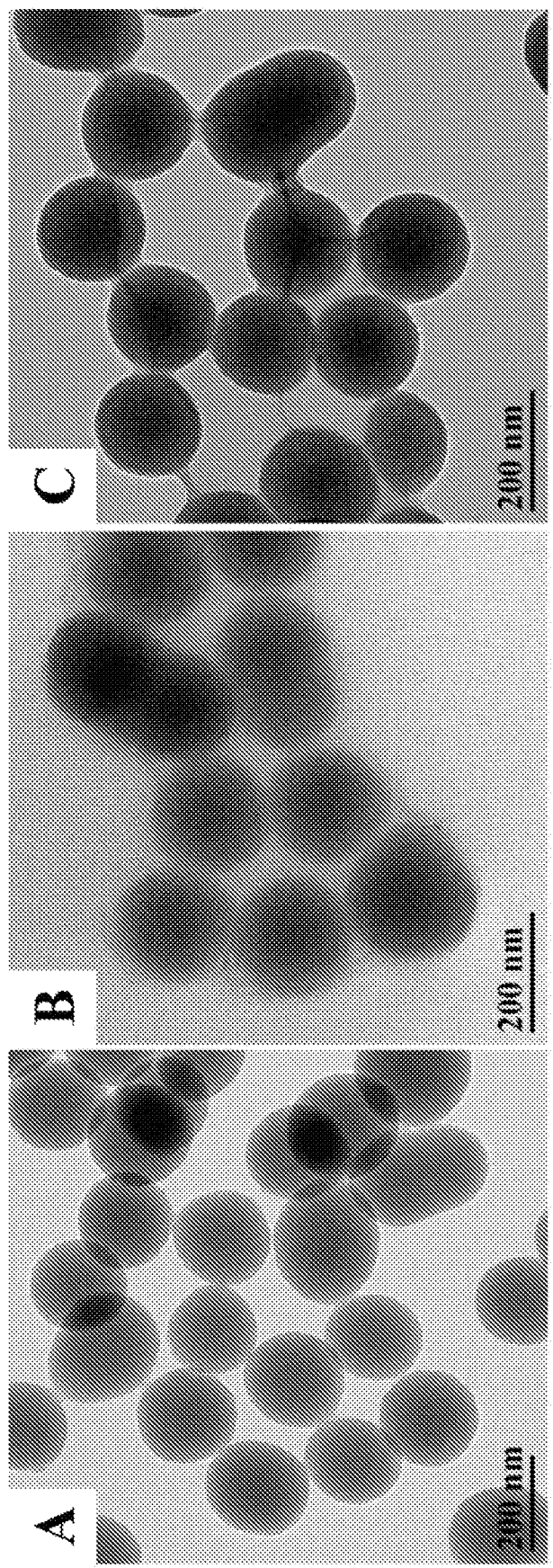
FIG. 6 shows transmission electron micrographs of 150 nm MSNs modified with (A) APTES; (B) BTMS; and (C) MPTMS. Particles in (A) exhibit smooth morphology, while agglomeration is observed in (B) and (C).
Figure 7:
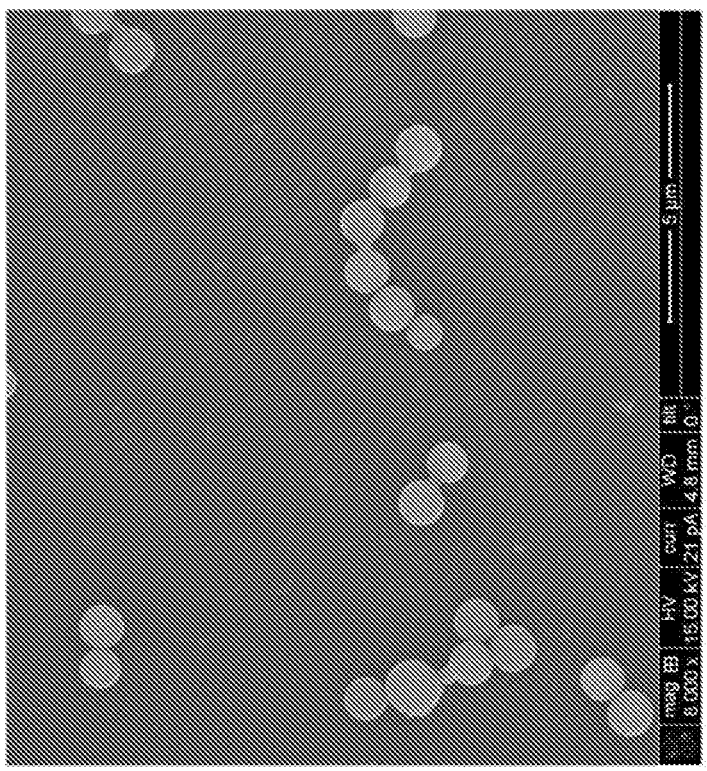
FIG. 7 shows scanning electron micrographs of 1100 nm AEAP3-modified particles with reactant AEAP3 concentrations of (A) 11.47 mM and (B) 14.34 mM. While the particles in (A) exhibited smooth morphology, undesirable particle agglomeration occurred at higher AEAP3 concentrations.
Figure 7:
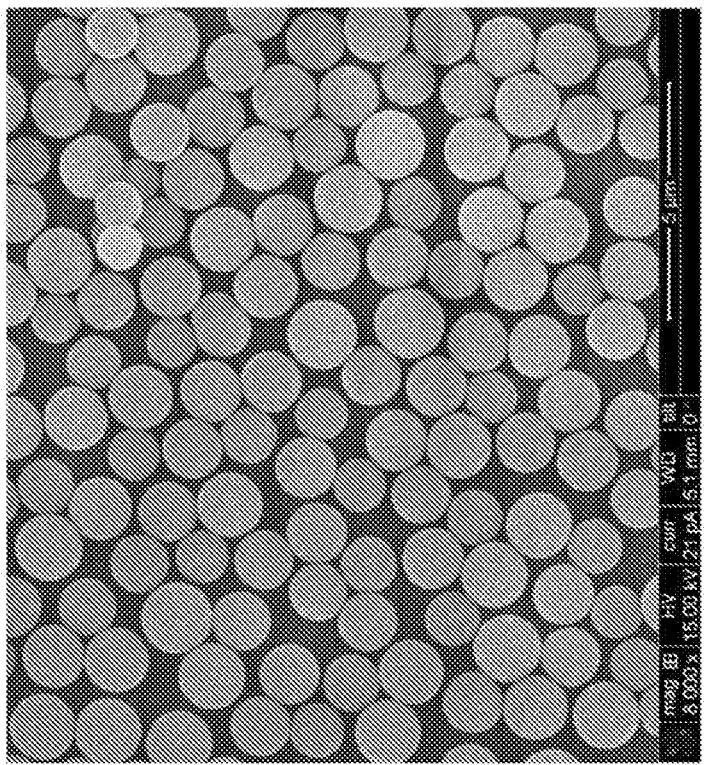

The morphology of the 150 nm APTES, BTMS, and MPTMS particles was examined using transmission electron microscopy (FIG. 6). As expected, 150 nm particles functionalized with APTES exhibited uniform morphology with excellent sphericity, consistent with the 150 nm AEAP3 MSNs. Evaluation of aqueous APTES particle suspensions by DLS indicated that the monodispersity of the particles (PDI=0.03±0.02) was preserved upon aminosilane modification. In contrast, undesirable silane bridging and particle agglomeration were evident in electron micrographs of the MPTMS- and BTMS-modified particles. A significant increase in the carbon wt % (measured by elemental analysis; Table 6) for all particle systems indicated that the silanes were incorporated into the final product. The morphological differences between particles observed using TEM were due to reaction with organosilanes. Accurate DLS analysis of the MPTMS and BTMS particle dispersions indicated significant sample polydispersity and agglomeration. While this data does not exclude the possibility of alternative reaction mechanisms, the particle analyses presented provide clear support of ion exchange reactions between cationic organosilanes and CTAB.

TABLE 5

Physicochemical characterization of 30 nm NO-releasing MSNs as a function of aminosilane modification.[a]

| Aminosilane Modification | Particle Characterization | | | | NO Release | | |
|---|---|---|---|---|---|---|---|
| | Geometric Size (nm)[b] | Z-average Size (nm)[c] | PDI[e] | Nitrogen wt %[d] | $t_{1/2}$ (min)[e] | $t_d$ (h)[f] | [NO]$_t$ (μmol mg$^{-1}$)[g] |
| MAP3 | 37.1 ± 8.3 | 91.2 ± 8.8 | 0.16 ± 0.05 | 3.26 ± 0.15 | 2.2 ± 0.2 | 1.8 ± 0.4 | 1.39 ± 0.10 |
| AHAP3 | 42.3 ± 8.1 | 131.8 ± 9.4 | 0.17 ± 0.04 | 4.18 ± 0.05 | 4.7 ± 2.3 | 5.9 ± 0.2 | 1.20 ± 0.10 |
| AEAP3 | 35.7 ± 8.1 | 74.1 ± 6.2 | 0.12 ± 0.06 | 4.65 ± 0.19 | 27.4 ± 8.9 | 12.2 ± 3.0 | 0.88 ± 0.05 |
| DET3 | 34.5 ± 7.6 | 83.0 ± 7.6 | 0.17 ± 0.04 | 5.60 ± 0.31 | 47.0 ± 11.9 | 33.2 ± 4.7 | 1.37 ± 0.19 |

[a]Error bars represent standard deviation for n > 3 separate syntheses.
[b]Estimated using electron micrographs.
[c]Measured via dynamic light scattering.
[d]Nitrogen wt % measured via elemental analysis.
[e]Half-life of NO release.
[f]NO-release duration; time required for NO concentrations to reach ≤10 ppb mg$^{-1}$.
[g]Total NO release.

TABLE 6 shows characterization of AEAP3-modified 100 nm mesoporous silica particles as a function of the reaction aminosilane concentration.[a]

| [AEAP3] (mM) | $t_{1/2}$ (min)[b] | $t_d$ (h)[c] | [NO]$_t$ (μmol mg$^{-1}$)[d] |
|---|---|---|---|
| 1.43 | 14.2 ± 1.6 | 7.2 ± 1.2 | 0.56 ± 0.09 |
| 2.87 | 15.8 ± 4.2 | 7.5 ± 0.3 | 0.69 ± 0.04 |
| 5.73 | 16.8 ± 4.1 | 9.0 ± 0.5 | 1.02 ± 0.04 |
| 11.47 | 25.6 ± 5.0 | 11.1 ± 0.7 | 1.41 ± 0.19 |

AMINOSILANE MODIFICATION AND NITRIC OXIDE-RELEASE KINETICS: As the structure of the precursor amine for N-diazeniumdiolate formation influences NO-release kinetics from both small molecules and nonporous silica particles, the NO-release kinetics from the MSNs were altered using different organosilanes. The 30 nm particle system was systematically modified with several aminosilanes, including AHAP3, DET3, and MAP3.

The characterization of the precursor- and NO donor-modified MSNs is provided in Table 5. Both the geometric size (~35-43 nm) and PDI (<0.20) of the particles remained approximately constant (p>0.5), indicating that the small particle size and monodispersity were preserved during the chemical modification regardless of aminosilane type. The measured hydrodynamic diameter (Z-average size) of each particle system (75-130 nm) was dependent on the composition of the aminosilane, but agreed well with the corresponding geometric sizes. The nitrogen wt % for each MSN system varied expectedly based on the elemental composition of the aminosilane reactant. Particles functionalized with the monoamine MAP3 incorporated the least amount of nitrogen (3.26%), while the nitrogen wt % was greatest for the triamine DET3 modification (5.60%). Intermediate nitrogen content was measured for MSNs with attached AHAP3 (4.18%) and AEAP3 (4.65%), which are diaminosilanes of differing carbon content.

Figure 8:
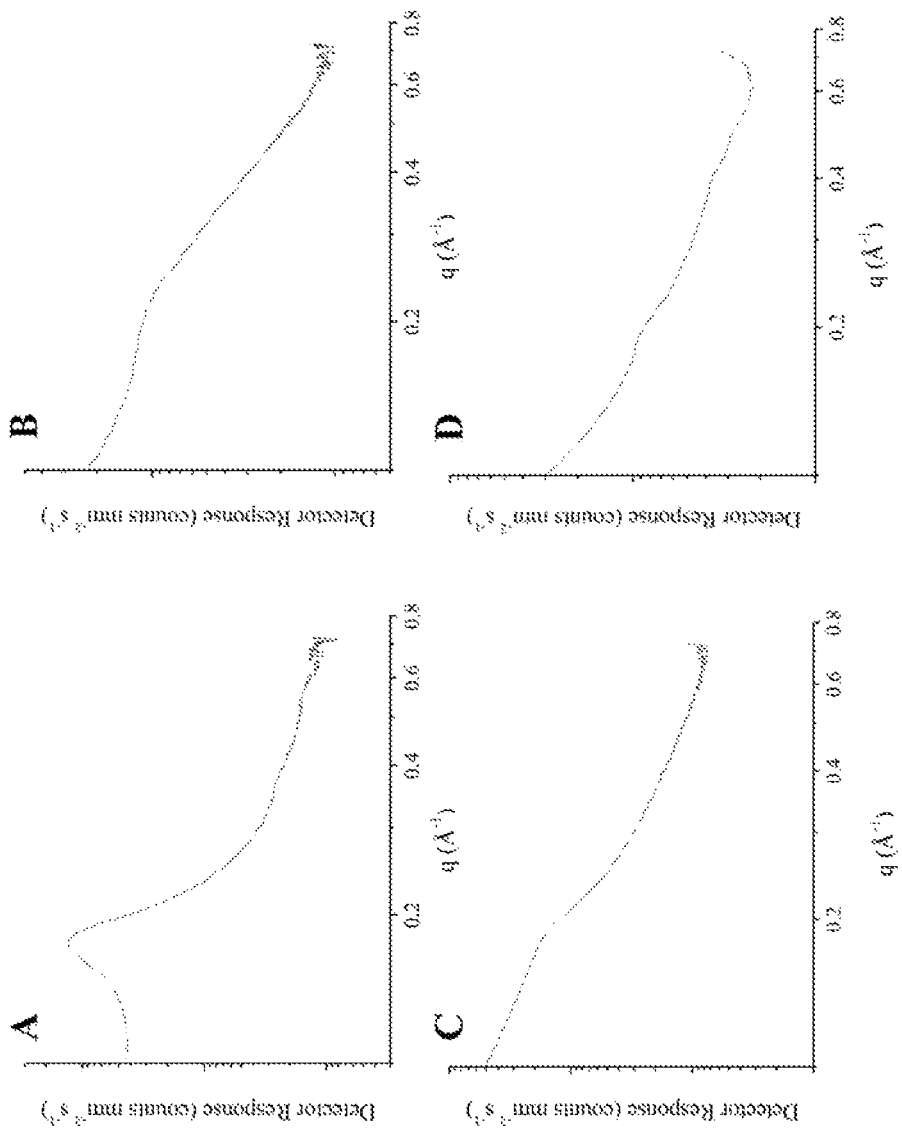
FIG. 8 shows small-angle X-ray scattering profile for AEAP3-modified (A) 1100 nm; (B) 450 nm; (C) 150 nm; and (D) 30 nm MSNs.
Figure 9:
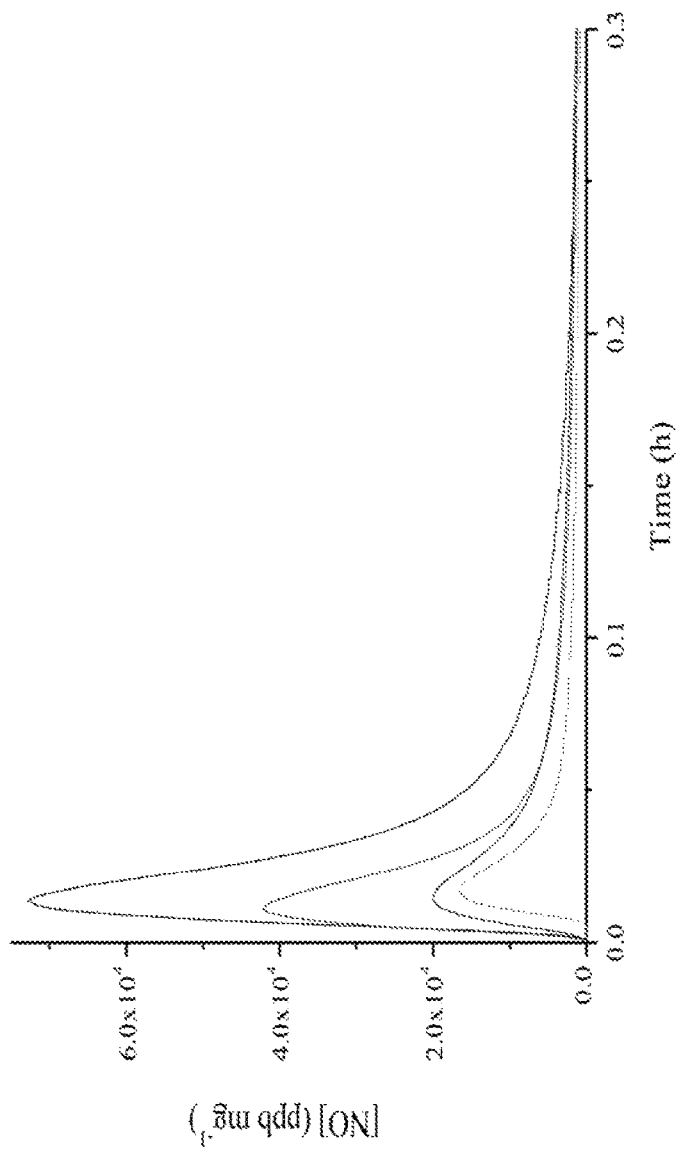
FIG. 9 shows real-time NO-release profiles for 30 nm MAP3/NO (black), AHAP3/NO (red), AEAP3/NO (green), and DET3/NO (blue) particles after ~20 min in PBS (pH 7.4) at 37° C.

The large degree of aminosilane incorporation translated to excellent particle NO storage, exceeding 1.00 μmol/mg for all particle systems tested except AEAP3/NO. The lower total NO storage for AEAP3/NO was expected based on previous results, as intramolecular hydrogen bonding between the side chain amines hinders N-diazeniumdiolate formation. While these interactions are also possible for DET3, the presence of two secondary amines resulted in greater NO storage. As expected, the MSN NO-release kinetics were markedly different between the four particle systems (p<0.01). The MAP3/NO and AHAP3/NO particles were characterized with rapid initial NO release (t½ of 2.2 and 4.7 min, respectively), while the NO release for the AEAP3/NO and DET3/NO particles was more sustained (t½ of 27.4 and 47.0 min, respectively) as a result of N-diazeniumdiolate charge stabilization by neighboring protonated amines (Table 5; FIG. 8). The NO-release durations covered ~2-33 h, rendering these particles especially useful as NO-delivery vehicles where tuning NO-release kinetics is critical to efficacy.

NO-release payloads, half-lives, and durations are all somewhat dependent on the particular synthesis (e.g., on the particle size and aminosilane used). However, typical NO storage values for the syntheses described herein are 0.8-1.6 umol/mg (with nothing lower than 0.8). The particles using the aminosilane MAP3 tended to store more NO (1.5-3.0 umol/mg) than using the other aminosilanes. For each size, one can tune the half-life and duration by the aminosilane identity—all of the syntheses are amenable to different amine modifications without changing the size/PDI. Particles modified with MAP3 release for 2-6 h and have half-lives of 2-5 min. AEAP3-based particles generally have half-lives in the range of 30-90 min and durations of 14-18 h regardless of particle size. DET3 gives the longest duration of release (33-50 h) with similar NO-release half-lives relative to the AEAP3 particles.

It should be noted that others have reported macromolecular NO donor scaffolds with total NO release values exceeding ~1.5 μmol/mg. For example, several porous metal organic frameworks (MOFs) have been developed which with NO storage approaching 1-7 μmol/mg through direct adsorption of NO gas. However, NO release from MOFs is generally rapid, restricting their utility to applications in which the NO donor scaffold is in contact with humidified gas. Both dendrimers and silica particles modified with S-nitrosothiol (RSNO) NO donors also exhibit large NO payloads (2 and 4 μmol/mg, respectively) with NO-release durations exceeding two days in deoxygenated PBS buffer. Unfortunately, RSNOs are unstable NO donors, readily decomposing to yield NO under multiple triggers (e.g., light, heat, reaction with Cu+ ions or ascorbate). S-nitrosothiol stability is further compromised in the presence of oxygen, where reaction with NO produces nitrogen trioxide, a RSNO-reactive species that initiates excessively rapid autocatalytic decomposition. In contrast, N-diazeniumdiolate NO donors alleviate the issue of uncontrolled decomposition, liberating NO at rates dependent on both the structure of the aminosilane and the solution pH. While poor NO storage and difficult synthetic procedures have traditionally excluded N-diazeniumdiolate-modified macromolecular NO donors from therapeutic evaluation, the preparation of NO-releasing mesoporous silica particles was achieved in high yields via ion exchange reactions. Excellent NO storage and diverse NO-release kinetics from the MSNs were obtained by simply changing the aminosilane without further synthetic optimization, representing a significant improvement to N-diazeniumdiolate-based NO-delivery vehicles.

In an embodiment, the present invention has elucidated to some extent the intricate relationships between pore ordering and NO-release kinetics. In one variation, the controlled mesophase structure should also provide an additional degree of control in macromolecular NO donor design. Moreover, the ability to easily modify the MSNs with different aminosilanes enabled tuning of NO-release kinetics without sacrificing control over either total NO storage or particle size. In an embodiment, the particles of the present invention should be useful for therapeutic utility. In one variation, the antibacterial action of the smaller 30 and 150 nm particles is postulated. The 450 and 1100 nm NO-releasing particles, while generally unsuitable as antimicrobials due to their large size, are postulated as being useful as dopants for NO-releasing polymer composites.

Experimental Section

MATERIALS: Tetraethylorthosilicate, 3-aminopropyltriethoxysilane, 3-mercaptopropyltrimethoxysilane, 3-(trimethoxysilylpropyl)diethylenetriamine, N-methylaminopropyltrimethoxysilane, N-(6-aminohexyl)aminopropyltrimethoxysilane, and N-(2-aminoethyl)-3-aminopropyltrimethoxysilane were purchased from Gelest (Morrisville, Pa.) and stored under nitrogen atmosphere. Sodium methoxide (NaOMe; 5.4 M in methanol), anhydrous N,N-dimethylformamide (DMF), anhydrous methanol (MeOH), ethanol (EtOH), aqueous ammonium hydroxide (30 wt %; $NH_4OH$), concentrated hydrochloric acid and all salts were purchased from Fisher Scientific (Fair Lawn, N.J.). Cetyltrimethylammonium bromide was purchased from Sigma (St. Louis, Mo.). Nitrogen ($N_2$), argon (Ar), and nitric oxide (NO) calibration (25.87 ppm in nitrogen) gases were purchased from Airgas National Welders (Raleigh, N.C.). Pure NO gas was purchased from Praxair (Danbury, Conn.). Water was purified using a Millipore Milli-Q UV Gradient A10 system (Bedford, Mass.) to a resistivity of 18.2 MΩ·cm and a total organic content of <10 ppb. Unless specified, all chemicals were used as received without further purification.

NANOPARTICLE SYNTHESIS: Tetraethylorthosilicate was added as a bolus to a stirred solution of water, EtOH, $NH_4OH$, and CTAB and allowed to react for 2 h. For the 30, 150, and 450 nm syntheses, 2.500 mL TEOS in EtOH (0.88, 1.06, and 1.33 M, respectively) was added to the reaction mixture, whereas 1.395 mL concentrated TEOS was used for the synthesis of the larger 1100 nm particles. Synthesis conditions for the MSNs are provided in Table 1. In all cases, reaction solutions appeared turbid within 15 min of silane introduction. Following particle formation, additional organosilane (AEAP3, AHAP3, APTES, BTMS, MAP3, MPTMS, or DET3) was introduced directly to the colloidal sol dropwise for 5 min using a Kent Scientific Genie Plus syringe pump (Torrington, Conn.). Elemental analysis of the 150 nm APTES, BTMS, and MPTMS particles are shown in table 7. The reaction was then aged overnight (~18 h) with stirring. Unless specified, an optimized TEOS:organosilane molar ratio of 1.56:1.00 was used. Following functionalization, particles were collected by centrifugation (6540 g, 4° C., 15 min), washed three times with EtOH, and dried under vacuum. For both the 30 and 150 nm particles, EtOH (one volume per two volumes of the reaction mixture) was added to the sol to induce particle flocculation during the collection procedure and enhance the overall yield. Bare MSNs were synthesized and collected similarly but without the organosilane functionalization step.

TABLE 7

Elemental analysis of 150 nm APTES, BTMS, and MPTMS particles.

| Silane Modification | Carbon wt % | Hydrogen wt % | Nitrogen wt % |
| --- | --- | --- | --- |
| APTES | 13.21 | 4.08 | 4.49 |
| BTMS | 23.16 | 4.79 | 0.16 |
| MPTMS | 25.58 | 4.84 | 0.88 |

Following MSN synthesis, residual CTAB was removed by ion exchange with hydrochloric acid (HCl). Particles (~200 mg) were suspended in 30 mL 10% v/v HCl in EtOH, agitated in an ultrasonicator bath for 30 min, and collected by centrifugation (6540 g, 4° C., 15 min). This process was repeated three times to ensure complete CTAB removal, followed by two additional EtOH washes. The particles were dried under vacuum to yield the pure nanoparticles. Typical yields for the amine-modified 30, 150, 450, and 1100 nm MSNs were 150, 175, 275, and 650 mg, respectively.

MESOPOROUS SILICA NANOPARTICLE CHARACTERIZATION: Particle morphology was characterized using a JEOL 2010F transmission electron microscope (Peabody, Mass.). Particles were suspended in MeOH at 1 mg/mL via brief agitation with an ultrasonicator. Subsequently, 5 µL of the resulting dispersion was cast onto a Formvar-coated copper grid (Ted Pella, Inc.; Redding, Calif.). The geometric size distribution of the particles was estimated from the electron micrographs using ImageJ software (Bethesda, Md.). The solution-phase behavior of the nanoparticles in water was investigated using dynamic light scattering (Malvern Zetasizer Nano-ZS; Westborough, Mass.) to determine MSN hydrodynamic diameter (Z-average size) and polydispersity index. Aqueous colloidal nanoparticle suspensions were prepared by dispersing particles at a concentration of 0.5 mg/mL using probe sonication at 7 W for 45 s using a Misonix S-4000 ultrasonicator (Farmingdale, N.Y.). Nitrogen sorption isotherms were collected on a Micromeritics Tristar II 3020 surface area and porosity analyzer (Norcross, Ga.). Samples were dried under a stream of $N_2$ gas at 110° C. overnight and then degassed for 2 h prior to analysis. Brunauer-Emmett-Teller (BET) analysis of physisorption data was used to calculate MSN specific surface area for $p/p^0$ values of 0.05-0.20. Pore size analysis using the adsorption branch of the sorption isotherm ($0.05<p/p^0<0.60$) was accomplished using the Barrett-Joyner-Halenda (BJH) method. Data obtained at relative pressures $>0.60$ $p/p^0$ were not considered for pore size determination as nitrogen capillary condensation occurred in the inter-particle volumes for the 30 nm and 150 nm particles, inflating the calculated pore width. Pore structure/ordering information was obtained by small-angle X-ray scattering analysis of the dry MSN powder. The Cu Kα line (1.54 Å) was used as the source radiation and scattering profiles were collected on a SAXSLab Ganesha point collimated pinhole system equipped with a moveable Dectris Pilatus 300K 2-dimensional single-photon-counting detector (Northampton, Mass.). Scattering vector (q) calibration was accomplished using the 1st-order ring for silver behenate, and data was collected for q-values of 0.005-0.724 $Å^{-1}$. Covalent incorporation of aminosilanes into the MSN backbone was confirmed via solid-state cross-polarization/magic angle spinning $(CP/MAS)^{29}Si$ nuclear magnetic resonance spectroscopy using a Bruker DMX 360 wide-bore spectrometer at a resonance frequency of 71.548 Hz. Samples were carefully ground in a mortar and pestle, packed into a 4 mm $ZrO_2$ rotor, and spun at 10 kHz. All chemical shifts were determined relative to an external tetramethylsilane standard. Elemental analysis was used to quantify the nitrogen weight percent of particles before and after functionalization with secondary amine-containing silanes using a Perkin Elmer 2400 CHNS/O analyzer (Waltham, Mass.) operated in CHN mode.

N-DIAZENIUMDIOLATE MODIFICATION AND NITRIC OXIDE RELEASE MEASUREMENTS: The aminosilane-modified MSNs (~15 mg) were suspended in 9:1 DMF:MeOH at 5 mg/mL in a glass vial and dispersed by ultrasonication for 20 min. After forming a homogeneous particle dispersion, NaOMe (5.4 M in MeOH; 9.0 µmol per mg MSN) was added to the solution and mixed. The MSN-containing vials were equipped with stir bars, placed in a stainless steel reaction bottle (Parr Instrument Co.; Moline, Ill.), and connected to an in-house NO reactor. The Parr bottle was flushed six times (three rapid, three 10 min) with 8 bar Ar gas to remove atmospheric oxygen and minimize the formation of NO byproducts. The vessel was subsequently pressurized with 10 bar NO gas and allowed to react for 72 h. Of note, the NO gas used for N-diazeniumdiolate formation was purified over solid potassium hydroxide for at least 4 h prior to reaction. After 72 h, the Parr bottle was vented and the vessel was flushed six more times (three short, three 10 min) to remove unreacted NO. The particles were again collected by centrifugation (6540 g, 4° C., 15 min), washed three times with EtOH, and dried under vacuum for 1-2 h. The resulting N-diazeniumdiolate-modified particles were stored in a vacuum-sealed bag at −20° C. until further use.

Nitric oxide release measurements were carried out using a Sievers 280i NO analyzer (Boulder, Colo.). Generation of NO from the proton-labile N-diazeniumdiolate NO donors was detected indirectly via chemiluminescence from excited state nitrogen dioxide formed upon the reaction of NO with ozone. The NOA was calibrated using a two-point linear calibration; air passed through a Sievers NO zero filter served as the blank value and 25.87 ppm NO in $N_2$ was used as the second calibration point. Particles (~1 mg) were added to the NOA sample flask containing 30 mL deoxygenated phosphate buffered saline (PBS, 0.010 M, pH 7.41) at 37° C. A stream of $N_2$ gas (80 mL/min) was continuously bubbled through solution to carry liberated NO to the analyzer. Supplemental nitrogen flow was provided to the flask to match the instrument collection rate of 200 mL/min. Instantaneous NO concentrations were measured at a sampling frequency of 1 Hz, providing near real-time information regarding MSN NO-release kinetics. The NO measurements were terminated when NO release from the particles was below 10 ppb/mg.

STATISTICAL ANALYSIS: One-way Analysis of Variance was used for multiple comparisons of MSN physicochemical properties (e.g., surface area, pore size, NO-release total amounts and kinetics) with provided p-values. Individual comparisons were carried out using a two-tailed Student's t-test with α=0.05 considered as the threshold for statistical significance.

In one embodiment, the present invention relates to ion exchange between cationic organosilanes and alkyltrimethylammonium SDAs (structure-directing agents), which represents a new MSN (mesoporous silica nanoparticle) functionalization approach.

In one embodiment, the organosilanes of the present invention are organoaminosilanes and they are used in cationic ion exchange and they are represented by the compounds of Formula I

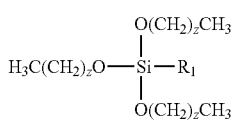

Formula I wherein z is 0, 1, or 2; and $R_1$ is

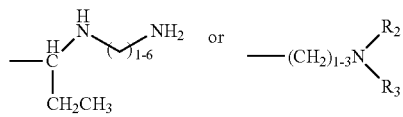

wherein $R_2$ and $R_3$ are each independently H, $CH_3$, $(CH_2)_{2-5}NH_2$, or $(CH_2)_{2-5}NH(CH_2)_{2-5}NH_2$.

In an embodiment, the organoaminosilanes are one or more of:

aminosilane N-(2-aminoethyl)-3-aminopropyltrimethoxysilane,
N-(6-aminohexyl)aminopropyl trimethoxysilane,
(3-Aminopropyl)triethoxysilane,
N-methylaminopropyltrimethoxysilane,
(3-trimethoxysilyl-propyl)diethylenetriamine or combinations thereof.

In an embodiment the present invention allows one to vary reaction conditions so as to get appropriately sized mesoporous silica nanoparticles. In an embodiment, the syntheses of the present invention allow controlled morphology wherein one can generate mesoporous silica nanoparticles with a useful surface area in the range of about 600-1400 $m^2/g$. Also, the synthetic conditions of the present invention allow one to attain particles with extremely ordered pore systems (for example either rods, or 2D hexagonal systems) to intermediate and more disordered pore systems (more typically). In an embodiment, the present invention allows one to produce particles with pore of a size of about 15-25 Å and with pore volumes of about 0.4-1.0 $cm^3/g$. In one embodiment, a synthesis of the present invention produces rods with much larger ordered pores in a size range of about 85-95 Å (for example, about 88 Å) ordered pores (2D hexagonal) with greater pore volumes of about 1.2-1.5 $cm^3/g$. Of note, generally pore volume correlates with pore size, so larger pores generally also yield greater pore volumes.

In an embodiment, the use of surfactant templated synthesis of mesoporous silica relies on silica formation around micelles. In a variation, using this synthetic method, one introduces 2-10 nm pores (e.g., cylindrical) into silica particles. In one variation, the interior (pore) surface can be chemically modified. For mesoporous silica, the surface area may be on the order of about 1,200 $m^2/g$, whereas it is on the order of less than about 200 $m^2/g$ for nonporous silica. The reported surface area measurements for the four particle systems described are 1170-1290 $m^2/g$. Reported surface area values are in the range of 700-1600 $m^2/g$, with 800-1000 $m^2/g$ being most common.

In an embodiment, a surfactant removal step is performed (e.g., agitation in ethanol/hydrochloric acid).

Using the ion exchange methods discussed herein, one is able to achieve a combination of features that cannot be achieved by using the methodologies of the prior art. For example, table 8 shows a comparison of the various methods that can be used to generate NO-releasing silica systems.

For example, and as shown in Table 8, the ion exchange methodology as described herein generates good NO storage capabilities, with a relative long NO-Release half life, wherein one can modulate size control. Moreover, there are few synthesis concerns as a one-pot reaction can be employed to generate these good NO-releasing silica systems. Because, the synthetic method is water-based, it is not subject to sensitivity to humidity unlike some of the other methodologies.

TABLE 8 comparison of different methods of generating NO-Releasing Silica Systems

| Synthesis | Porosity | NO Storage ($\mu$mol mg$^{-1}$) | NO-Release Half-Life (h) | Size Control? | Synthesis Concerns | Reference(s) |
| --- | --- | --- | --- | --- | --- | --- |
| Co-condensation | Nonporous | 0.05-0.68 | 0.7-6.0 | No | None | J. Am. Chem. Soc. 2007, 4612-4619 |
| Co-condensation | Nonporous | 0.22-0.39 | 0.1-2.0 | No | None | J. Dent. Res. 2014, 1089-1094 J. Dent. Res. 2015, 1092-1098 |
| Grafting | Nonporous | 0.24-0.70 | 0.1-0.8 | Yes | Water sensitive | ACS Appl. Mater. Interfaces 2013, 9322-9329 Small 2013, 2189-2198 |
| Grafting | Nonporous | 0.26-0.53 | ~0.9 h | Yes | Water Sensitive | J. Am. Chem. Soc. 2003, 5015-5024 |
| Co-condensation | Nonporous | 0.27-0.30 | Not reported | No | None | Biomacromolecules 2012, 3334-3342 |
| Microemulsion (hybrid) | Nonporous | 1.00-1.49 | ~2-3 h | Yes | 500 mL alcohol solvent 10 mg yield 2 d synthesis | ACS Nano 2011, 7235-7244 |
| Ion Exchange | Mesoporous | 0.80-2.90 | 0.2-5.4 | Yes | None | ACS Appl. Mater. Interfaces 2016, 2220-2231 |

In an embodiment, the present invention relates to a method of producing NO-releasing mesoporous silica particles, wherein said method comprises:
generating a mesoporous silica particle by reacting tetraalkoxysilanes or alkoxysilanes with a cetyltrimethylammonium halide to generate a cetyltrimethylammonium ion.

In a variation, the present invention relates to reacting tetraethylorthosilicate with a cetyltrimethylammonium halide to generate a cetyltrimethylammonium ion; exchanging via an ion exchange reaction the cetyltrimethylammonium ion for an organosilane molecule.

Other tetraalkoxysilanes or alkoxysilanes that may be used in the present invention include tetraethylorthosilicate, or methyltrimethoxysilane, ethyltrimethoxysilane, propyltrimethoxysilane, isopropyltrimethoxysilane, butyltrimethoxysilane, isobutyltrimethoxysilane, and t-butyltrimethoxysilane (i.e., alkoxysilanes with a single alkyl chain side group).

In one variation, the cetyltrimethylammonium halide may be cetyltrimethylammonium bromide.

In a variation, the ion exchange reaction is a cation exchange reaction.

In an embodiment, the organosilane is an organoaminosilane and the organoaminosilane may be a compound of Formula I:

$$H_3C(CH_2)_zO-\underset{\underset{O(CH_2)_zCH_3}{|}}{\overset{\overset{O(CH_2)_zCH_3}{|}}{Si}}-R_1$$

Formula I wherein z is 0, 1, or 2; and $R_1$ is $$-\underset{\underset{CH_2CH_3}{|}}{\overset{\overset{H}{|}}{C}}\overset{H}{\underset{}{\diagdown}}\overset{}{\underset{}{N}}\diagup\diagdown_{1-6}NH_2 \quad or \quad -(CH_2)_{1-3}N\overset{R_2}{\diagdown}_{R_3}$$

and wherein $R_2$ and $R_3$ are each independently H, $CH_3$, $(CH_2)_{2-5}NH_2$, or $(CH_2)_{2-5}NH(CH_2)_{2-5}NH_2$.

In one variation, the organoaminosilane may be one or more of:
aminosilane N-(2-aminoethyl)-3-aminopropyltrimethoxysilane,
N-(6-aminohexyl)aminopropyl trimethoxysilane,
(3-Aminopropyl)triethoxysilane, N-methylaminopropyltrimethoxysilane, and
(3-trimethoxysilyl-propyl)diethylenetriamine or combinations thereof.

In one variation of the method, the method further comprises charging the NO-releasing mesoporous silica particles with NO.

In an embodiment, the NO-releasing mesoporous silica particles have many advantages such as:
a) produce consistent NO-releasing mesoporous silica particles morphology regardless of aminosilane incorporation b) allow for a one-pot synthesis of amine-functionalized NO-releasing mesoporous silica particles c) produce NO-releasing mesoporous silica particles that are insensitive to ambient humidity and d) provide NO-releasing mesoporous silica particles wherein aminosilane incorporation is reproducible.

In one variation, the method allows one to realize all of the advantages. In one variation of the method, the generation of mesoporous silica particles can be procured in a one-pot reaction process.

In one variation, the size of the NO-releasing mesoporous silica particles is between about 30 nm and 1100 nm. In one variation, the NO-releasing mesoporous silica particles are substantially monodisperse in size. To determine the meaning of substantially monodisperse in size, one should look to the error and/or standard deviation parameters as enumerated above, wherein standard statistical methods are used to determine the extent of deviation from the various sized NO-releasing mesoporous silica particles that have been made. In one embodiment, substantially monodisperse in size means that the appropriately numbered NO-releasing mesoporous silica particles are within one standard deviation unit in a normal distribution curve (e.g., using standard statistical methods).

In one variation, the method relates to varying a combination of a concentration of the cetyltrimethylammonium halide and a temperature of a reaction to generate the NO-releasing mesoporous silica particles that are substantially monodisperse in size. The reaction conditions (e.g., concentration and temperature) predominantly determine the size NO-releasing mesoporous silica particles that are generated.

In one variation, the NO-releasing mesoporous silica particles are of a size that is one of about 30 nm, 150 nm, 350 nm and/or 1100 nm.

The present invention is not just related to methods but also to NO-releasing mesoporous silica particles that have special properties. For example, in one embodiment, the NO-releasing mesoporous silica particles can be charged with NO at a concentration of at least about 0.4 μmol/mg and release NO with a half-life for release of the NO that is no less than about 2 minutes or alternatively, 10 minutes, or alternatively, about 15 minutes, or alternatively, about 20 minutes, or alternatively, about 25 minutes. In a variation, the NO-releasing mesoporous silica particles are substantially monodisperse in size.

In one variation, the NO-releasing mesoporous silica particles are of a size that is one of about 30 nm, 150 nm, 350 nm and/or 1100 nm.

The present invention also relates to the generation of NO-releasing mesoporous silica particles by a process that comprises generating a mesoporous silica particle by reacting tetraethylorthosilicate with a cetyltrimethylammonium halide to generate a cetyltrimethylammonium ion; and exchanging via an ion exchange reaction the cetyltrimethylammonium ion for an organosilane molecule.

In one variation, the organosilane is a compound of Formula I:

$$H_3C(CH_2)_zO-\underset{\underset{O(CH_2)_zCH_3}{|}}{\overset{\overset{O(CH_2)_zCH_3}{|}}{Si}}-R_1$$

Formula I wherein z is 0, 1, or 2; and $R_1$ is $$-\underset{\underset{CH_2CH_3}{|}}{\overset{\overset{H}{|}}{C}}\overset{H}{\underset{}{\diagdown}}\overset{}{\underset{}{N}}\diagup\diagdown_{1-6}NH_2 \quad or \quad -(CH_2)_{1-3}N\overset{R_2}{\diagdown}_{R_3}$$

and wherein $R_2$ and $R_3$ are each independently H, $CH_3$, $(CH_2)_{2-5}NH_2$, or $(CH_2)_{2-5}NH(CH_2)_{2-5}NH_2$.

In a variation, the organosilane may be one or more of: aminosilane N-(2-aminoethyl)-3-aminopropyltrimethoxysilane, N-(6-aminohexyl)aminopropyl trimethoxysilane, (3-Aminopropyl)triethoxysilane, N-methylaminopropyltrimethoxysilane, and (3-trimethoxysilyl-propyl)diethylenetriamine or combinations thereof.

It should be understood that the present invention is not to be limited by the above description. Modifications can be made to the above without departing from the spirit and scope of the invention. It is contemplated and therefore within the scope of the present invention that any feature that is described above can be combined with any other feature that is described above (even if those features are not described together). Moreover, it should be understood that the present invention contemplates and it is therefore within the scope of the invention that any step, element or feature can be added and/or omitted in the methods to obtain the NO-releasing mesoporous silica nanoparticles of the present invention. In any event, the scope of protection to be afforded is to be determined by the claims which follow and the breadth of interpretation which the law allows.

We claim:

1. A method of producing nitric oxide (NO)-releasing mesoporous silica particles, wherein said method comprises:
    reacting an alkoxysilane with an alkylammonium surfactant in the absence of added organoaminosilane to form a turbid mixture comprising mesoporous silica nanoparticles (MSN) in a colloidal sol;
    adding an organoaminosilane to the MSN in the colloidal sol to modify the MSN via an ion exchange reaction of the organoaminosilane and an alkylammonium ion and form amino-functionalized MSN; and
    reacting the amino-functionalized MSN with NO gas to produce NO-releasing MSN.

2. The method of claim 1, wherein the alkoxysilane is one or more of tetraethylorthosilicate, methyltrimethoxysilane, ethyltrimethoxysilane, and isobutyltrimethoxysilane and the alkylammonium surfactant is a cetyltrimethylammonium halide.

3. The method of claim 2, wherein the cetyltrimethylammonium halide is cetyltrimethylammonium bromide.

4. The method of claim 1, wherein the ion exchange reaction is a cation exchange reaction.

5. The method of claim 1, wherein the organoaminosilane is a compound of Formula I:

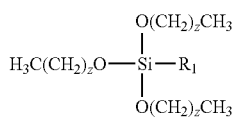

Formula I wherein z is 0, 1, or 2; and $R_1$ is

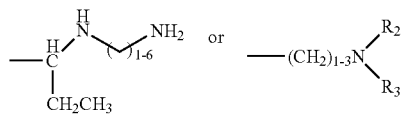

wherein $R_2$ and $R_3$ are each independently H, $CH_3$, $(CH_2)_{2-5}NH_2$, or $(CH_2)_{2-5}NH(CH_2)_{2-5}NH_2$.

6. The method of claim 1, wherein the organoaminosilane is one or more of:
    N-(2-aminoethyl)-3-aminopropyltrimethoxysilane,
    N-(6-aminohexyl)aminopropyl trimethoxysilane,
    (3-Aminopropyl)triethoxysilane,
    N-methylaminopropyltrimethoxysilane,
    and
    (3-trimethoxysilyl-propyl)diethylenetriamine or combinations thereof.

7. The method of claim 1, wherein the method produces the NO-releasing MSN via a one-pot synthesis.

8. The method of claim 1, wherein the NO-releasing MSN have a diameter-between about 30 nm and 1100 nm.

9. The method of claim 1, wherein the NO-releasing MSN are substantially monodisperse in size.

10. The method of claim 1, wherein the NO-releasing MSN have a diameter of about 30 nm, 150 nm, 350 nm and/or 1100 nm.

11. The method of claim 1, wherein the alkylammonium surfactant is:
    a. a linear alkylammonium salt having a structure of: $[C_nH_{2n+1}(CH_3)_3N]^+$ $Br^-$ or $[C_nH_{2n+1}(C_2H_5)_3N]^+$ $Br^-$ where n=8, 10, 12, 14, 16, 18, 20, 22;
    b. a geminal salt having a structure of: $[C_nH_{2n+1}(CH_3)_2N-(CH_2)_s-N(CH_3)_2-C_mH_{m+1}]^+$ $Br^-$ where n=m=12, 14, 16, 18, 20, 22 and s=2-12; or
    c. a divalent surfactant having a structure of: $[C_nH_{2n+1}(CH_3)_2N-C_mH_{2m+1}(CH_3)_3N]^{2+}$ where n+m=8, 10, 12, 14, 16, 18, 20, 22.

12. The method of claim 1, wherein the NO-releasing MSN are insensitive to ambient humidity.

13. The method of claim 1, wherein the amino-functionalized MSN have a polydispersity index (PDI) of less than 0.20.

14. A method of producing nitric oxide (NO)-releasing mesoporous silica particles, wherein said method comprises:
    reacting an alkoxysilane with an alkylammonium surfactant to form mesoporous silica nanoparticles (MSN) in a colloidal sol;
    adding an organoaminosilane to the MSN in the colloidal sol to exchange via an ion exchange reaction of the organoaminosilane and an alkylammonium ion to form amino-functionalized MSN; and
    reacting the amino-functionalized MSN with NO gas to produce NO-releasing MSN,
    wherein the amino-functionalized MSN have a polydispersity index (PDI) of less than 0.20.

15. A method of producing nitric oxide (NO)-releasing mesoporous silica particles, wherein said method comprises:
    reacting an alkoxysilane with an alkylammonium surfactant to form mesoporous silica nanoparticles (MSN) in a colloidal sol;
    adding an organoaminosilane to the MSN in the colloidal sol to exchange via an ion exchange reaction of the organoaminosilane and an alkylammonium ion to form amino-functionalized MSN; and
    reacting the amino-functionalized MSN with NO gas to produce NO-releasing MSN;
    wherein the alkoxysilane and the alkylammonium surfactant are reacted for at least 15 minutes before the addition of the organoaminosilane.

* * * * *

UNITED STATES PATENT AND TRADEMARK OFFICE
CERTIFICATE OF CORRECTION

PATENT NO. : 11,420,986 B2
APPLICATION NO. : 15/772759
DATED : August 23, 2022
INVENTOR(S) : Mark H. Schoenfisch and Robert J. Soto It is certified that error appears in the above-identified patent and that said Letters Patent is hereby corrected as shown below:

In the Specification

At Column 6, Line 32, "methyl aminopropyl-trimethoxysilane (MAP3)" should read
-- methylaminopropyl-trimethoxysilane (MAP3) --.

At Column 12, Table 5, footnote $f$, "$\leq 10$ ppb mg$^{-1}$" should read -- $<10$ ppb mg$^{-1}$ --.

In the Claims

At Claim 11, Column 22, Lines 26-27, "b. a geminal salt having a structure of:
[$C_nH2_{n+1}(CH_3)_2N$–$(CH_2)_s$–$N(CH_3)_2$–$C_mH_{m+1}$]+ Br$^-$" should read
-- b. a geminal salt having a structure of: [$C_nH2_{n+1}(CH_3)_2N$–$(CH_2)_s$–$N(CH_3)_2$–$C_mH_{2m+1}$]+ Br$^-$ --.

Signed and Sealed this
Fourteenth Day of February, 2023

Katherine Kelly Vidal
*Director of the United States Patent and Trademark Office*